United States Patent
Ellingsen et al.

(10) Patent No.: US 7,192,445 B2
(45) Date of Patent: Mar. 20, 2007

(54) MEDICAL PROSTHETIC DEVICES AND IMPLANTS HAVING IMPROVED BIOCOMPATIBILITY

(75) Inventors: Jan Eirik Ellingsen, Bekkestua (NO); Staale Petter Lyngstadaas, Nesoddtangen (NO)

(73) Assignee: Astra Tech AB, Molndal (SE)

( * ) Notice: Subject to any disclaimer, the term of this patent is extended or adjusted under 35 U.S.C. 154(b) by 0 days.

(21) Appl. No.: 10/010,140

(22) Filed: Dec. 6, 2001

(65) Prior Publication Data
US 2002/0111694 A1 Aug. 15, 2002

Related U.S. Application Data

(60) Provisional application No. 60/254,987, filed on Dec. 12, 2000.

(30) Foreign Application Priority Data

Dec. 6, 2000 (DK) ............................ 2000 01829

(51) Int. Cl.
| | |
|---|---|
| A61B 17/56 | (2006.01) |
| A61F 2/02 | (2006.01) |
| A61F 2/08 | (2006.01) |
| A61F 2/44 | (2006.01) |
| A61F 2/28 | (2006.01) |
| A61F 2/30 | (2006.01) |
| B05D 3/12 | (2006.01) |

(52) U.S. Cl. ................ 623/11.11; 623/1.1; 623/2.1; 623/16.11; 623/23.53; 623/23.57; 623/23.6; 606/60; 606/67; 606/69; 606/76

(58) Field of Classification Search ............. 623/1.1, 623/2.1, 11.11, 16.11, 23.53, 23.57, 23.76, 623/23.6; 606/60, 61, 67, 69, 76; 427/327, 427/2.1, 2.24

See application file for complete search history.

(56) References Cited

U.S. PATENT DOCUMENTS

| | | | |
|---|---|---|---|
| 4,542,539 A | | 9/1985 | Rowe, Jr. et al. |
| 4,818,559 A | * | 4/1989 | Hama et al. ............... 427/2.27 |
| 5,152,993 A | * | 10/1992 | Bjursten et al. ............ 424/422 |
| 5,383,935 A | | 1/1995 | Shirkhanzadeh |
| 6,190,412 B1 | * | 2/2001 | Lee et al. ................. 623/16.11 |
| 6,627,321 B1 | * | 9/2003 | Ellingsen et al. ............ 428/469 |

FOREIGN PATENT DOCUMENTS

| | | |
|---|---|---|
| EP | 0212929 A2 | 3/1987 |
| EP | 0264354 A2 | 4/1988 |
| RU | 2074674 C1 | 3/1997 |
| WO | WO 97/27821 | 8/1997 |
| WO | WO 00/38753 | 7/2000 |

OTHER PUBLICATIONS

Aronsson, B.-O et al., "Hydrogen desorption from sand-blasted and acid-etched titanium surfaces after glow-discharge treatment," *Journal of Biomedical Materials Research*, vol. 54:20-29 (2001).
Taborelli, M. et al., "Influence of surface treatments developed for oral implants on the physical and biological properties of titanium," *Clinical Oral Implants Research*, vol. 8:208-216 (1997).
Conforto, E. et al., "Crystallographic properties and mechanical behaviour of titanium hydride layers grown on titanium implants," *Philosophical Magazine*, vol. 84(7):631-645 (Mar. 2004).

* cited by examiner

*Primary Examiner*—David J. Isabella
(74) *Attorney, Agent, or Firm*—Birch, Stewart, Kolasch & Birch

(57) ABSTRACT

Disclosed are medical prosthetic devices or medical implants which exhibit improved biocompatitibly. The devices or implants include a metal material, e.g. titanium, in which the metal surface parts are coated with a corresponding hydride material that contains one or more biomolecule substance. This biomolecule substance may contain one or more biologically active molecules, e.g. bioadhesives, biopolymers, blood proteins, enzymes, extra cellular matrix proteins, extra cellular matrix biomolecules, growth factors and hormones, peptide hormones, deoxyribonucleic acids, ribonucleic acids, receptors, enzyme inhibitors, drugs, biologically active anions and cations, vitamins, adenosine monophosphate (AMP), adenosine diphosphate (ADP), adenosine triphosphate (ATP), marker biomuolecules, amino acids, fatty acids, nucleotides (RNA and DNA bases), or sugars.

18 Claims, No Drawings

MEDICAL PROSTHETIC DEVICES AND IMPLANTS HAVING IMPROVED BIOCOMPATIBILITY

RELATED APPLICATIONS

This application claims priority to U.S. Provisional Application No. 60/254,987, entitled "Medical Prosthetic Devices and Implants Having Improved Biocompatibility" filed on Dec. 12, 2000; and Denmark Patent Application PA 2000, 01829, entitled "Medical Prosthetic Devices and Implants Having Improved Biocompatibility" filed on Dec. 6, 2000; the entire contents of both of which are hereby incorporated herein by reference.

FIELD OF THE INVENTION

The present invention concerns medical prosthetic devices and implants having improved biocompatibility.

BACKGROUND OF THE INVENTION

It has been proposed to improve the biocompatibility of e.g. a titanium prosthesis by coating metal surfaces thereof with a layer of titanium hydride. Such a hydride layer may be applied by plasma bombardment, or in may be applied by electrolysis, see for example U.S. patent application Ser. No. 09/868,965 which is hereby incorporated by reference.

It has also been proposed to improve the biocompatibility of prostheses or implants by binding or integrating various active biomolecules to the surface of the prosthesis, e.g. on to the metallic surface of a titanium prosthesis. It has been the aim with implants prepared this way that they have improved fit; exhibit increased tissue stickiness and increased tissue compatibility; have a biologically active surface for increased cell growth, differentiation and maturation; exhibit reduced immunoreactivity; exhibit antimicrobial activity; exhibit increased biomineralisation capabilities; result in improved wound and/or bone healing; lead to improved bone density; have reduced "time to load" and cause less inflammation.

Such binding has often been proposed carried out using for example chemical reactants having two reactive functionalities such as formalin or glutaraldehyde, but the reactive nature of these agents often leads to the biomolecules becoming biologically inactive and/or with enhanced immunoreactivity which is undesirable.

SUMMARY OF THE INVENTION

It has now surprisingly been found that it is possible to interlock, bind, trap and/or integrate a wide variety of biomolecules in or with a hydride layer during the inorganic process of formation of such a hydride layer on metals by electrolysis. Prior to this observation it was considered very difficult to bind and stabilize unmodified, bioactive biomolecules on metals, especially for use as bioactive surfaces on metals for use as implants in the vertebrate body in vivo.

The invention therefore concerns a medical prosthetic device or implant containing a metal material (A) selected from the group consisting of titanium or an alloy thereof, zirconium or an alloy thereof, tantalum or an alloy thereof, hafnium or an alloy thereof, niobium or an alloy thereof and a chromium-vanadium alloy, wherein surface parts of the metal material (A) are coated with a layer of a corresponding hydride material (B) selected from titanium hydride, zirconium hydride, tantalum hydride, hafnium hydride, niobium hydride and chromium and/or vanadium hydride, respectively, characterised in that the layer of hydride material (B) comprises one or more biomolecule substances (C) associated therewith.

The invention further concerns a method for preparing a medical prosthetic device or implant as defined above, said method comprising subjecting surface parts of the metal material (A) as defined above to an electrolysis treatment to form the layer of hydride material (B), said electrolysis treatment being carried out in the presence of one or more biomolecule substances (C).

DETAILED DESCRIPTION OF THE INVENTION

In the present context, the phrase "medical prosthetic device and implant" includes within its scope any device intended to be implanted into the body of a vertebrate animal, in particular a mammal such as a human. Non-limiting examples of such devices are medical devices that replaces anatomy or restores a function of the body such as the femoral hip joint; the femoral head; acetabular cup; elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stapes, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices.

In the present context, the term "biomolecule" is intended to cover and comprise within its meaning a very wide variety of biologically active molecules in the widest sense of the word, be they natural biomolecules (i.e. naturally occurring molecules derived from natural sources), synthetic biomolecules (i.e. naturally occurring molecules prepared synthetically as well as non-naturally occurring molecules or forms of molecules prepared synthetically) or recombinant biomolecules (i.e. prepared through the use of recombinant techniques).

A non-limiting list of main groups of and species biomolecules that are contemplated as being suitable for incorporation into a metal hydride layer (in a stable and/or physiologically reversible manner) in accordance with the invention is given below.

Extracted Biomolecules

Bioadhesives:

These are biomolecules that mediate attachment of cells, tissue, organs or organisms onto non-biological surfaces like glass, rock etc. This group of bio-molecules includes the marine mussel adhesive proteins, fibrin-like proteins, spider-web proteins, plant-derived adhesives (resins), adhesives extracted from marine animals, and insect-derived adhesives (like resilins). Some specific examples of adhesives are:

Fibrin; fibroin; *Mytilus edulis* foot protein (mefp1, "mussel adhesive protein"); other mussel's adhesive proteins; proteins and peptides with glycine-rich blocks; proteins and peptides with poly-alanine blocks; and silks.

Cell Attachment Factors:

Cell attachment factors are biomolecules that mediate attachment and spreading of cells onto biological surfaces or other cells and tissues. This group of molecules typically contains molecules participating in cell-matrix and cell-cell interaction during vertebrate development, neogenesis, regeneration and repair. Typical biomolecules in this class are molecules on the outer surface of cells like the CD class of receptors on white blood cells, immuneglobulins and haemagglutinating proteins, and extracellular matrix molecules/ligands that adhere to such cellular molecules. Typical examples of cell attachment factors with potential for use as bioactive coating on metal hydride-coated implants are: Ankyrins; cadherins (Calcium dependent adhesion molecules); connexins; dermatan sulphate; entactin; fibrin; fibronectin; glycolipids; glycophorin; glycoproteins; heparan sulphate; heparin sulphate; hyaluronic acid; immunglobulins; keratan sulphate; integrins; laminins; N-CAMs (Calcium independent Adhesive Molecules); proteoglycans; spektrin; vinculin; vitronectin.

Biopolymers:

Biopolymers are any biologically prepared molecule which, given the right conditions, can be assembled into polymeric, macromolecular structures. Such molecules constitute important parts of the extracellular matrix where they participate in providing tissue resilience, strength, rigidity, integrity etc. Some important biopolymers with potential for use as bioactive coating on metal hydride-coated implants are: Alginates; Amelogenins; cellulose; chitosan; collagen; gelatins; oligosaccharides; pectin.

Blood Proteins:

This class of proteins typically contains any dissolved or aggregated protein which normally is present whole blood. Such proteins can participate in a wide range of biological processes like inflammation, homing of cells, clotting, cell signalling, defence, immune reactions, metabolism etc. Typical examples with potential for use as bioactive coating on metal hydride-coated implants are: Albumin; albumen; cytokines; factor IX; factor V; factor VII; factor VIII; factor X; factor XI; factor XII; factor XIII; hemoglobins (with or without iron); immunoglobulins (antibodies); fibrin; platelet derived growth factors (PDGFs); plasminogen; thrombospondin; transferrin.

Enzymes:

Enzymes are any protein or peptide that have a specific catalytic effect on one ore more biological substrates which can be virtually anything from simple sugars to complex macromolecules like DNA. Enzymes are potentially useful for triggering biological responses in the tissue by degradation of matrix molecules, or they could be used to activate or release other bioactive compounds in the implant coating. Some important examples with potential for use as bioactive coating on metal hydride-coated implants are: Abzymes (antibodies with enzymatic capacity); adenylate cyclase; alkaline phosphatase; carboxylases; collagenases; cyclooxygenase; hydrolases; isomerases; ligases; lyases; metallomatrix proteases (MMPs); nucleases; oxidoreductases; peptidases; peptide hydrolase; peptidyl transferase; phospholipase; proteases; sucrase-isomaltase; TIMPs; transferases.

Extracellular Matrix Proteins and Biomolecules:

Specialized cells, e.g. fibroblasts and osteoblasts, produce the extracellular matrix. This matrix participates in several important processes. The matrix is crucial for i.a. wound healing, tissue homeostasis, development and repair, tissue strength, and tissue integrity. The matrix also decides the extracellular milieu like pH, ionic strength, osmolarity etc. Furthermore extracellular matrix molecules are crucial for induction and control of biomineral formation (bone, cartilage, teeth). Important extracellular proteins and biomolecules with potential for use as bioactive coating on metal hydride-coated implants include: Ameloblastin; amelin; amelogenins; collagens (I to XII); dentin-sialo-protein (DSP); dentin-sialo-phospho-protein (DSPP); elastins; enamelin; fibrins; fibronectins; keratins (1 to 20); laminins; tuftelin; carbohydrates; chondroitin sulphate; heparan sulphate; heparin sulphate; hyaluronic acid; lipids and fatty acids; lipopolysaccharides.

Growth Factors and Hormones:

Growth factors and hormones are molecules that bind to cellular surface structures (receptors) and generate a signal in the target cell to start a specific biological process. Examples of such processes are growth, programmed cell death, release of other molecules (e.g. extracellular matrix molecules or sugar), cell differentiation and maturation, regulation of metabolic rate etc. Typical examples of such biomolecules with potential for use as bioactive coating on metal hydride-coated implants are: Activins (Act); Amphiregulin (AR); Angiopoietins (Ang 1 to 4); Apo3 (a weak apoptosis inducer also known as TWEAK, DR3, WSL-1, TRAMP or LARD); Betacellulin (BTC); Basic Fibroblast Growth Factor (bFGF, FGF-b); Acidic Fibroblast Growth Factor (aFGF, FGF-a); 4-1BB Ligand; Brain-derived Neurotrophic Factor (BDNF); Breast and Kidney derived Bolokine (BRAK); Bone Morphogenic Proteins (BMPs); B-Lymphocyte Chemoattractant/B cell Attracting Chemokine 1 (BLC/BCA-1); CD27L (CD27 ligand); CD30L (CD30 ligand); CD40L (CD40 ligand); A Proliferation-inducing Ligand (APRIL); Cardiotrophin-1 (CT-1); Ciliary Neurotrophic Factor (CNTF); Connective Tissue Growth Factor (CTGF); Cytokines; 6-cysteine Chemokine (6Ckine); Epidermal Growth Factors (EGFs); Eotaxin (Eot); Epithelial Cell-derived Neutrophil Activating Protein 78 (ENA-78); Erythropoietin (Epo); Fibroblast Growth Factors (FGF 3 to 19); Fractalkine; Glial-derived Neurotrophic Factors (GDNFs); Glucocorticoid-induced TNF Receptor Ligand (GITRL); Granulocyte Colony Stimulating Factor (G-CSF); Granulocyte Macrophage Colony Stimulating Factor (GM-CSF); Granulocyte Chemotactic Proteins (GCPs); Growth Hormone (GH); I-309; Growth Related Oncogene (GRO); Inhibins (Inh); Interferon-inducible T-cell Alpha Chemoattractant (I-TAC); Fas Ligand (FasL); Heregulins (HRGs); Heparin-Binding Epidermal Growth Factor-Like Growth Factor (HB-EGF); fms-like Tyrosine Kinase 3 Ligand (Flt-3L); Hemofiltrate CC Chemokines (HCC-1 to 4); Hepatocyte Growth Factor (HGF); Insulin; Insulin-like Growth Factors (IGF 1 and 2); Interferon-gamma Inducible Protein 10 (IP-10); Interleukins (IL 1 to 18); Interferon-gamma (IFN-gamma); Keratinocyte Growth Factor (KGF); Keratinocyte Growth Factor-2 (FGF-10); Leptin (OB); Leukemia Inhibitory Factor (LIF); Lymphotoxin Beta (LT-B); Lymphotactin (LTN); Macrophage-Colony Stimulating Factor (M-CSF); Macrophage-derived Chemokine (MDC); Macrophage Stimulating Protein (MSP); Macrophage Inflammatory Proteins (MIPs); Midkine (MK); Monocyte Chemoattractant Proteins (MCP-1 to 4); Monokine Induced by IFN-gamma (MIG); MSX 1; MSX 2; Mullerian Inhibiting Substance (MIS); Myeloid Progenitor Inhibitory Factor 1 (MPIF-1); Nerve Growth Factor (NGF); Neurotrophins (NTs); Neutrophil Activating Peptide 2 (NAP-2); Oncostatin M (OSM); Osteocalcin; OP-1; Osteopontin; OX40 Ligand;

Platelet derived Growth Factors (PDGF aa, ab and bb); Platelet Factor 4 (PF4); Pleiotrophin (PTN); Pulmonary and Activation-regulated Chemokine (PARC); Regulated on Activation, Normal T-cell Expressed and Secreted (RANTES); Sensory and Motor Neuron-derived Factor (SMDF); Small Inducible Cytokine Subfamily A Member 26 (SCYA26); Stem Cell Factor (SCF); Stromal Cell Derived Factor 1 (SDF-1); Thymus and Activation-regulated Chemokine (TARC); Thymus Expressed Chemokine (TECK); TNF and ApoL-related Leukocyte-expressed Ligand-1 (TALL-1); TNF-related Apoptosis Inducing Ligand (TRAIL); TNF-related Activation Induced Cytokine (TRANCE); Lymphotoxin Inducible Expression and Competes with HSV Glycoprotein D for HVEM T-lymphocyte receptor (LIGHT); Placenta Growth Factor (PlGF); Thrombopoietin (Tpo); Transforming Growth Factors (TGF alpha, TGF beta 1, TGF beta 2); Tumor Necrosis Factors (TNF alpha and beta); Vascular Endothelial Growth Factors (VEGF-A,B,C and D); calcitonins; and steroid compounds such as naturally occurring sex hormones such as estrogen, progesterone, testosterone as well as analogues thereof. Thus, certain implants such as IUD's (intrauterine devices) comprising e.g. estrogens or progesterone or analogues thereof could be contemplated.

Nucleic Acids (DNA):

DNA encodes the genes for proteins and peptides. Also, DNA contains a wide array of sequences that regulate the expression of the contained genes. Several types of DNA exist, depending on source, function, origin, and structure. Typical examples for DNA based molecules that can be utilized as bioactive, slow release coatings on implants (local gene-therapy) are: A-DNA; B-DNA; artificial chromosomes carrying mammalian DNA (YACs); chromosomal DNA; circular DNA; cosmids carrying mammalian DNA; DNA; Double-stranded DNA (dsDNA); genomic DNA; hemi-methylated DNA; linear DNA; mammalian cDNA (complimentary DNA; DNA copy of RNA); mammalian DNA; methylated DNA; mitochondrial DNA; phages carrying mammalian DNA; phagemids carrying mammalian DNA; plasmids carrying mammalian DNA; plastids carrying mammalian DNA; recombinant DNA; restriction fragments of mammalian DNA; retroposons carrying mammalian DNA; single-stranded DNA (ssDNA); transposons carrying mammalian DNA; T-DNA; viruses carrying mammalian DNA; Z-DNA.

Nucleic Acids (RNA):

RNA is a transcription of DNA-encoded information. (Sometimes (in some viruses) RNA is the essential information-encoding unit). Besides being an intermediate for expression of genes, RNA have been shown to have several biological functions. Ribozymes are simple RNA molecules with a catalytic action. These RNA can catalyze DNA and RNA cleavage and ligation, hydrolyze peptides, and are the core of the translation of RNA into peptides (the ribosome is a ribozyme). Typical examples of RNA molecules with potential for use as bioactive coating on metal hydride-coated implants are: Acetylated transfer RNA (activated tRNA, charged tRNA); circular RNA; linear RNA; mammalian heterogeneous nuclear RNA (hnRNA), mammalian messenger RNA (mRNA); mammalian RNA; mammalian ribosomal RNA (rRNA); mammalian transport RNA (tRNA); mRNA; poly-adenylated RNA; ribosomal RNA (rRNA); recombinant RNA; retroposons carrying mammalian RNA; ribozymes; transport RNA (tRNA); viruses carrying mammalian RNA.

Receptors:

Receptors are cell surface biomolecules that bind signals (e.g. hormone ligands and growth factors) and transmit the signal over the cell membrane and into the internal machinery of cells. Different receptors are differently "wired" imposing different intracellular responses even to the same ligand. This makes it possible for the cells to react differentially to external signals by varying the pattern of receptors on their surface. Receptors typically bind their ligand in a reversible manner, making them suitable as carriers of growth factors that are to be released into the tissue. Thus by coating implants with growth factor receptors, and then load these receptors with their principal ligands, a bioactive surface is achieved that can be used for controlled release of growth factors to the surrounding tissues following implantation. Examples of suitable receptors with potential for use as bioactive coating on metal hydride-coated implants includes: The CD class of receptors CD; EGF receptors; FGF receptors; Fibronectin receptor (VLA-5); Growth Factor receptor, IGF Binding Proteins (IGFBP 1 to 4); Integrins (including VLA 1-4); Laminin receptor; PDGF receptors; Transforming Growth Factor alpha and beta receptors; BMP receptors; Fas; Vascular Endothelial Growth Factor receptor (Flt-1); Vitronectin receptor.

Synthetic Biomolecules:

Synthetic biomolecules are molecules that are based on (mimicking) naturally occurring biomolecules. By synthesizing such molecules a wide array of chemical and structural modification can be introduced that can stabilize the molecule or make it more bioactive or specific. Thus if a molecule is either too unstable or unspecific to be used from extracts it is possible to engineer them and synthesize them for use as implant surface coatings. Furthermore, many biomolecules are so low abundant that extraction in industrial scales is impossible. Such rare biomolecules have to be prepared synthetically, e.g. by recombinant technology or by (bio-) chemistry. Below is listed several classes of synthetic molecules that can be potentially useful for implant coatings:

Synthetic DNA:

A-DNA; antisense DNA; B-DNA; complimentary DNA (cDNA); chemically modified DNA; chemically stabilized DNA; DNA; DNA analogues; DNA oligomers; DNA polymers; DNA-RNA hybrids; double-stranded DNA (dsDNA); hemi-methylated DNA; methylated DNA; single-stranded DNA (ssDNA); recombinant DNA; triplex DNA; T-DNA; Z-DNA.

Synthetic RNA:

Antisense RNA; chemically modified RNA; chemically stabilized RNA; heterogeneous nuclear RNA (hnRNA); messenger RNA (mRNA); ribozymes; RNA; RNA analogues; RNA-DNA hybrids; RNA oligomers; RNA polymers; ribosomal RNA (rRNA); transport RNA (tRNA).

Synthetic Biopolymers:

Cationic and anionic liposomes; cellulose acetate; hyaluronic acid; polylactic acid; polyglycol alginate; polyglycolic acid; poly-prolines; polysaccharides.

Synthetic Peptides:

Decapeptides containing DOPA and/or diDOPA; peptides with sequence "Ala Lys Pro Ser Tyr Pro Pro Thr Tyr Lys"; peptides where Pro is substituted with hydroxyproline; peptides where one or more Pro is substituted with DOPA; peptides where one or more Pro is substituted with diDOPA; peptides where one or more Tyr is substituted with DOPA;

peptide hormones; peptide sequences based on the above listed extracted proteins; peptides containing an RGD (Arg Gly Asp) motif.

Recombinant Proteins:

All recombinantly prepared peptides and proteins

Synthetic Enzyme Inhibitors:

Synthetic enzyme inhibitors range from simple molecules, like certain metal ions, that block enzyme activity by binding directly to the enzyme, to synthetic molecules that mimic the natural substrate of an enzyme and thus compete with the principle substrate. An implant coating including enzyme inhibitors could help stabilizing and counteract breakdown of other biomolecules present in the coating, so that more reaction time and/or higher concentration of the bioactive compound is achieved. Examples of enzyme inhibitors are: Pepstatin; poly-prolines; D-sugars; D-aminocaids; Cyanide; Diisopropyl fluorophosphates (DFP); metal ions; N-tosyl-1-phenylalaninechloromethyl ketone (TPCK); Physostigmine; Parathion; Penicillin.

Vitamins (Synthetic or Extracted) For Incorporation in Hydride:

Biotin; calciferol (Vitamin D's; vital for bone mineralisation); citrin; folic acid; niacin; nicotinamide; nicotinamide adenine dinucleotide (NAD, NAD+); nicotinamide adenine dinucleotide phosphate (NADP, NADPH); retinoic acid (vitamin A); riboflavin; vitamin B's; vitamin C (vital for collagen synthesis); vitamin E; vitamin K's.

Other Bioactive Molecules For Incorporation Into Hydride:

Adenosine di-phosphate (ADP); adenosine mono-phosphate (AMP); adenosine triphosphate (ATP); amino acids; cyclic AMP (cAMP); 3,4-dihydroxyphenylalanine (DOPA); 5'-di(dihydroxyphenyl-L-alanine (diDOPA); diDOPA quinone; DOPA-like o-diphenols; fatty acids; glucose; hydroxyproline; nucleosides; nucleotides (RNA and DNA bases); prostaglandin; sugars; sphingosine 1-phosphate; rapamycin; synthetic sex hormones such as estrogen, progesterone or testosterone analogues, e.g. Tamoxifene; estrogen receptor modulators (SERMs) such as Raloxifene; bis-phosphonates such as alendronate, risendronate and etidronate; statins such as cerivastatin, lovastatin, simvaststin, pravastatin, fluvastatin, atorvastatin and sodium 3,5-dihydroxy-7-[3-(4-fluorophenyl)-1-(methylethyl)-1H-indol-2-yl]-hept-6-enoate.

Drugs For Incorporation Into Hydride Coatings:

Drugs incorporated in the hydride layer could be utilized for local effects like improving local resistance against invading microbes, local pain control, local inhibition of prostaglandin synthesis; local inflammation regulation, local induction of biomineralisation and local stimulation of tissue growth. Examples of drugs suitable for incorporation into metal hydride layers include: Antibiotics; cyclooxygenase inhibitors; hormones; inflammation inhibitors; NSAID's; painkillers; prostaglandin synthesis inhibitors; steroids, tetracycline (also as biomineralizing agent).

Biologically Active Ions For Incorporation In Hydride Coatings:

Ions are important in a diversity of biological mechanisms. By incorporating biologically active ions in metal hydride layers on implants it is possible to locally stimulate biological processes like enzyme function, enzyme blocking, cellular uptake of biomolecules, homing of specific cells, biomineralization, apoptosis, cellular secretion of biomolecules, cellular metabolism and cellular defense. Examples of bioactive ions for incorporation into metal hydride include: Calcium; chromium; copper; fluoride; gold; iodide; iron; potassium; magnesium; manganese; selenium; silver; sodium; zinc.

Marker Biomolecules:

Biological Markers are molecules that generates a detectable signal, e.g. by emitting light, enzymatic activity, radioactivity, specific color, magnetism, x-ray density, specific structure, antigenicity etc., that can be detected by specific instruments or by microscopy or an imaging method like x-ray or magnetic resonance. Markers are used to monitor biological processes in research and development of new biomedical treatment strategies. On implants, such markers would typically be employed to monitor processes like biocompatibility, formation of tissue, tissue neogenesis, biomineralisation, inflammation, infection, regeneration, repair, tissue homeostasis, tissue breakdown, tissue turnover, release of biomolecules from the implant surface, bioactivity of released biomolecules, uptake and expression of nucleic acids released from the implant surface, and antibiotic capability of the implant surface to provide "proof of principle", effect, efficacy and safety validation prior to clinical studies.

Marker biomolecules suitable for incorporation in hydride coatings include: Calcein; alizaran red; tetracyclins; fluorescins; fura; luciferase; alkaline phosphatase; radiolabeled aminoacids (e.g. marked with $^{32}P$, $^{33}P$, $^{3}H$, $^{35}S$, $^{14}C$, $^{125}I$, $^{51}Cr$, $^{45}Ca$); radiolabeled nucleotides (e.g. marked with $^{32}P$, $^{33}P$, $^{3}H$, $^{35}S$, $^{14}C$,); radiolabeled peptides and proteins; radiolabeled DNA and RNA; immuno-gold complexes (gold particles with antibodies attached); immuno-silver complexes; immuno-magnetite complexes; Green Fluorescent protein (GFP); Red Fluorescent Protein (E5); biotinylated proteins and peptides; biotinylated nucleic acids; biotinylated antibodies; biotinylated carbon-linkers; reporter genes (any gene that generates a signal when expressed); propidium iodide; diamidino yellow.

The device or implant according to the invention can be used for a number of purposes. Examples of such purposes include use for: inducing local hard tissue (e.g. bone tissue) formation at the implantation site; controlling microbial growth and/or invasion at the implantation site or systemically; reducing inflammation at the implantation site or systemically; stimulating ligament repair, regeneration or formation; inducing cartilage formation; nucleating, controlling and/or templating biomineralization; improving attachment between implants and tissues; improving osseointegration of implants; improving tissue adherence to an implant; hindering tissue adherence to an (semi-permanent or temporary) implant; improving contact between tissues or tissues and implants, improving tissue sealing of a (surgical) wound; inducing apoptosis (cell death) in unwanted cells (e.g. cancer cells); inducing specific cell differentiation and/or maturation, increasing tissue tensile strength; improving wound healing; speeding up wound healing; templating tissue formation; guiding tissue formation; local gene therapy; stimulating nerve growth; improving vascularisation in tissues adjacent to an implant; stimulating local extracellular matrix synthesis; inhibiting local extracellular matrix breakdown; inducing local growth factor release; increasing local tissue metabolism; improving function of a tissue or body-part; reducing local pain and discomfort. The purpose will depend on the type of implant as well as the nature and/or concentration of the biomolecule present in the hydride layer on the implant.

When the metal material (A) is an alloy of titanium, zirconium, tantalum, hafnium or niobium, it may be an alloy between one or more of these metal elements; or it may be an alloy containing one or more other metals such as aluminium, vanadium, chrome, cobalt, magnesium, iron, gold, silver, copper, mercury, tin or zinc; or both.

It is preferred that the metal material (A) is titanium or an alloy thereof, e.g. an alloy with zirconium, tantalum, hafnium, niobium, aluminium, vanadium, chrome, cobalt, magnesium, iron, gold, silver, copper, mercury, tin or zinc. In a particularly preferred embodiment, the metal material (A) is titanium.

The corresponding hydride material (B) is preferably titanium hydride.

The amount of biomolecule substance (C) present on or in the hydride layer (B) of the parts of the prosthesis, device or implant coated with the hydride may vary within wide limits, e.g. dependent on the chemical and biological characteristics of the biomolecule substance or substances in question. Thus, the biomolecule substance (C) associated with the hydride material (B) may be present in amounts ranging from as low from 1 picogram per $mm^2$ to as high as 1 mg per $mm^2$ of hydride-coated device or implant surface. However, it is contemplated that most useful biomolecule coatings will range from 0.1 nanogram to 100 microgram per $mm^2$.

As indicated above, the method of the invention involves subjecting surface parts of the metal material (A) to a electrolysis treatment to form the hydride layer (B), said treatment being carried out in the presence of one or more biomolecule substances as discussed above. It has been found that is important that the conditions in the electrolyte (pH, ionic strength etc.) are such that the biomolecule has a net positive charge. It is therefore advantageous that most biomolecules are ampholytes, i.e. they are weak acids (or bases) that change their net charge according to the ionic strength and pH of the solution they are dissolved in. Consequently, the main concern for incorporation thereof in a hydride layer is stability under the conditions needed for bio-hydride preparation, i.e. an environment that supply enough $H^+$ ions for hydride preparation and at the same time keeps the net charge of the biomolecule in question positive. This mostly means that the electrolyte should have a high salt concentration and hence ionic strength; a comparatively high temperature, although preferably below any denaturing temperature of the biomolecule substance; and a low pH.

Thus, the electrolyte may be any salt solution, preferably aqueous, e.g. a solution of sodium chloride, sodium sulphate, calcium phosphate, calcium chloride, phosphate buffered saline (PBS), saline, a salt solution mimicking physiological conditions, bicarbonates, carbonates etc., in which the desired biomolecule is dissolved. The ionic strength of the salt is typically 1M, but concentrations can be adjusted to as low as 0,01 M and as high as 10 M according to the chemical properties and concentration of the biomolecule(s).

The temperature of the electrolyte containing the biomolecule may range from ambient (20° C.) to as high as the boiling point of the electrolyte, typically around 100° C., although the use of temperatures in the upper part of this range clearly depends on the ability of the biomolecule to withstand such temperatures without damage. If the biomolecule can withstand it, an optimum temperature for the formation of hydride is around 80° C.

The pH of the electrolyte is typically adjusted to the desired pH by means of a strong acid, e.g. HCl, HF, $H_2SO_4$ etc. although it should be taken into account that a pH below 2 will produce a irregular, corroded implant surface on titanium while a pH above 2 conserves the original surface. The pH is adjusted according to the desired Hydride/biomolecule ratio; Low pH produces an implant surface with a high hydride/biomolecule ratio (=more metal hydride), whereas a high pH close to the pI of the biomolecule in question will produce a surface with a low hydride/biomolecule ratio (=more biomolecules). Accordingly, while any pH between 0 and 10 can be used, the preferred pH for hydride preparation is between 5 and 2, depending on the chemical characteristics and concentration of the biomolecule(s), the electrolyte used and the preferred hydride/biomolecule ratio. For higher hydride/biomolecule(s) ratios (=more hydride), adjust pH more acidic, for lower hydride/biomolecule(s) ratios (=more biomolecule(s)) adjust pH closer to, but not above, $pI_{BIOMOLECULE}$. The only requirement is that there are hydrogen ions ($H^+$) and positively charged biomolecules (Biomolecule$^+$, net charge) present in the electrolyte.

The concentration of the biomolecule(s) (one or any combinations of two or more) in the electrolyte may vary over a very wide range, depending on type of bioactivity, type of molecule, chemical and biological characteristics, toxicity, potency, mode of action, if it is to be released or not from the hydride layer, stability in vivo, stability in the electrolyte, availability, optimal pH, etc., Thus, the concentration of the biomolecule(s) in the electrolyte may be within the range of 1 pg to 50 mg per milliliter. A preferred range is between 10 pg and 1 mg per milliliter, but the optimal biomolecule concentration should always be by finally determined in pilot experiments with each biomolecule or biomolecule-mix. Also, the time span over which the electrolysis is performed may vary but chiefly influences the thickness of the hydride layer and hence the concentration of biomolecules in the hydride layer.

An electrolysis cell for use in the method of the invention may be of any conventional design but is typically a two-chamber cell without any conducting connections between the chambers except for the electrolyte. The metal implant to be hydride-modified is placed in the cathode (i.e. the negatively charged electrode) chamber whereas the anode (the positively charged electrode), typically made of carbon, is placed in a separate chamber. The electrolytes of each chamber are connected through a porous glass or porcelain filter allowing the current to pass unhindered but without any exchange of electrolytes between the two chambers. This is important because the products from the anode reaction, e.g. chloride or hypo-chlorites etc, could potentially interfere with the formation of the biomolecule-hydride layer or destroy or modify the biomolecule in the cathode electrolyte. The separation of the two cells also allows the use of a smaller cathode electrolyte volume and thus a more effective use of biomolecules as well as the possibility to use a two-electrolyte system that allows optimization of the electrolytic process, e.g. one electrolyte optimal for biomolecules on the cathode side and an electrolyte on the anode side which is optimized for the efficacy of the electrolysis per se (conductivity, avoiding toxic products, or even producing useful byproducts/coatings).

As indicated above, the temperature in the cathode cell ($T_{cat}$) should be as high at possible with an optimum for hydride preparation at 80° C.

The electrolytic process itself also produces heat which can pose two problems; constituents of the electrolyte will evaporate so that the volume decreases and the ionic strength and the concentration of biomolecules increase above the preferred range, and the increase in temperature might cause precipitation, coagulation, denaturation, degradation or destruction of the biomolecule(s) present. Therefore, the cathode compartment of the electrolysis cell is preferably equipped with a cooled lid for condensation of vaporized electrolyte and a temperature regulated radiator shell for stabilizing temperatures and volumes during electrolysis.

By adjusting current, charge and electrolyte composition it may also be possible to provide a favorable milieu for positive charge for most biomolecules. If not, a pulse field electrolysis set-up where the polarity of the electrodes is switching in controlled cycles during preparation of the bio-hydride layer could be one way to omit a negative net charge problem.

The power supply is typically a so-called current pump, i.e. a device delivering a constant current even if the resistance within the circuit varies. Although voltages between 0,1 and 1000 volts can be used, the voltage is typically below 10 volts. The current density during electrolysis is typically in the range of 0,1 mA to 1 A per square centimeter ($cm^2$) of implant specimen. A preferred charge density is 1 $mA/cm^2$ although adjustments in the electrolyte, pH and temperature to increase biomolecule compatibility may command minor or major deviations from this value.

The duration of the process depends on several parameters such as the desired thickness of the bio-hydride layer, the composition and characteristics of the electrolyte, the characteristics of the biomolecule, the temperature and pH, the desired hydride/biomolecule ratio, the size of the implant specimen, the volume of the cathode electrolyte, the concentration of the biomolecule, etc. Thus, the duration of the process may be between 0.5 hors and several days. However, an optimal time-span is generally between 8 and 24 hours.

To monitor the bio-hydride process, a calomel electrode may typically be placed in the cathode chamber. When the hydride layer formation process at the cathode is optimal, a difference of −1 Volt is observed between the calomel electrode and the cathode. If the current differs much from this value, the process will be running under sub-optimal conditions and a change in the set-up should be considered. Furthermore, a temperature probe and a pH probe may typically be placed in the cathode chamber to monitor that the process is running within the desired pH and temperature limits. A stirring device such as a magnetic stirrer may also be applied in the cathode cell to continuously mix the electrolyte and keep the temperature homogenous and avoid variations in local ionic strength, pH and biomolecule concentrations.

fter the electrolysis step, the now biomolecule/hydride-coated metal device or implant is immediately removed from the electrolyte and treated according to the requirement of the biomolecule(s) in question. Typically, the device or implant specimen is allowed to air-dry and is then packaged in a sterile, airtight plastic bag in which it is stored until use for implantation. However, some biomolecules might be sensitive to drying, and consequently a wet storage system might be desired, e.g. like canning or storage in a fluid like saline or simply the electrolyte from the manufacturing process. Although the electrolysis can be run under aseptic or even sterile conditions, the need for doing this may be avoided by including a sterilization step prior to use, using conventional methods such as ionizing radiation, heating, autoclaving, or ethylene oxide gas etc. The choice of method will depend on the specific characteristics and properties of the biomolecule(s) present in the metal hydride layer.

Prior to the electrolysis treatment, the device or implant should be thoroughly cleaned. This may typically consist in the implant being mechanically pre-treated by electropolishing or sandblasting to modify surface structure if desired, and subsequently thoroughly cleaned using hot caustic soda followed by a de-greasing step, e.g. in concentrated tri-chloro-ethylene, ethanol or methanol, before being treated in a pickling solution, e.g. hydrofluoric acid, to remove oxides and impurities on the surface. After pickling the implant specimen is washed thoroughly in hot, double distilled, ion-exchanged water.

he invention is further illustrated by the following, non-limiting examples of which Examples 1–4 describe conducted experiments, and Examples 5–11 illustrate contemplated working examples.

EXAMPLE 1

Preparation of a titanium hydride implant surface layer containing an extracellular matrix protein.

A two-chamber electrolysis cell was used to prepare a layer of titanium hydride containing the extracellular matrix molecule amelogenin onto five coin-shaped electropolished titanium implants each with a surface area of 0.6 $cm^2$ exposed to the electrolyte. Five similar items were used as controls by being present in the electrolyte chamber, but not connected to the electrolysis current. The electrolyte in both chambers was 1M NaCl in sterile water, pH adjusted to pH 4 by the use of HCl, and the initial concentration of amelogenin was 0.1 mg/ml. For electrolysis a voltage of 10 volts at a charge density of 1 $mA/cm^2$ was used. The temperature of the cathode chamber was set to 70° C. Electrolysis was allowed to progress for 18 hours after which the titanium implants were removed from the electrolysis cell, washed in sterile water and allowed to air-dry in a desiccator.

After drying the titanium test and control specimens were each washed three times in 1 ml saline at pH 6.5. Following the washes, any protein remaining on the titanium surfaces was dissolved by boiling the titanium specimen in 0.5 ml 2×SDS-PAGE sample buffer (0.4 g SDS, 1.0 g 2-mercaptoethanol, 0.02 g bromophenol blue and 4.4 g glycerol in 10 ml 0.125 M Tris/HCl, pH 6.8). The washing solutions and the 2×SDS-PAGE sample buffer with possible protein therein were precipitated with an equal volume of 0.6 N perchloric acid and the supernatant was cleared by centrifugation. The precipitation pellets, containing salt and possible organic molecules, were then dissolved in 50 μl 2×SDS-PAGE sample buffer and boiled for five minutes. All samples were then submitted to electrophoresis on a 12% SDS-polyacrylamide gel at 80 mA overnight. After electrophoresis, proteins in the gel were transferred onto a poly(vinylidene difluoride) membrane by the semi-dry "sandwich" electroblotting technique. Amelogenin proteins were then detected by an immune assay using an rabbit amelogenin specific primary IgG antibody and a biotin labelled goat anti rabbit IgG secondary antibody. The western blot showed significant amounts of amelogenins present in extracts from test specimens, and hence trapped in the titanium hydride layer thereon, whereas no amelogenins were detected in extracts from the control specimens that were not connected to the electrolysis current.

This experiment clearly demonstrates that a significant amount of amelogenin was incorporated in the hydride layer during the electrolytic process. The amelogenin proteins were not merely present as a simple coating, since there is no evidence of proteins in the initial washing solutions. Only with the combination of a strong detergent (SDS), a reducing agent (mercaptoethanol) and high temperature (100° C.) could amelogenins be extracted from the titanium hydride surface layer and detected by western blot. The amount of protein extracted was calculated to be 50 μg/$cm^2$ by comparison with an amelogenin standard. This figure is well within the bioactivity range of this extracellular matrix protein.

EXAMPLE 2

Production of an amelogenin-containing titanium hydride implant surface layer.

The set-up from example one was used to produce a layer of titanium hydride containing the extracellular matrix molecule amelogenin onto electropolished titanium implants with a surface area of 0.35 cm$^2$ exposed to the electrolyte. The electrolyte in both chambers was 1M NaCl in sterile water, pH adjusted to pH 4 by the use of HCl, and the initial concentration of amelogenin was 0.1 mg/ml. For electrolysis a voltage of 10 volts at a charge density of 1 mA/cm$^2$ was used. $T_{cat}$ was set to 70° C. Electrolysis was allowed to progress for 18 hours after which the titanium implants were removed from the electrolysis cell, washed in sterile water and allowed to air-dry in a desiccator.

After drying the titanium specimens were washed three times in 1 ml saline at pH 6.5. Following the washes the proteins remaining on the titanium surfaces were dissolved by boiling the titanium specimen in 0.1 ml 2×SDS sample buffer (0.4 g SDS, 1.0 g 2-mercaptoethanol in 10 ml 0.125 M Tris/HCl, pH 6.8) for 5 minutes. The amount of amelogenin dissolved into the SDS solution from the rinsed titanium surfaces was then analyzed by standard photometry measuring light absorbance at 280 and 310 nm against a 2×SDS sample buffer blank, and comparing the results with a standard dilution series of amelogenin in 2×SDS sample buffer. The experiment was repeated twice in series of 16 implants, both times with 5 negative internal controls in the form of identical titanium implants that was present in the reaction chamber during the whole process, but not attached to the cathode.

This experiment clearly demonstrates that a significant amount of amelogenin was incorporated in the hydride layer during the electrolytic process. The amelogenin proteins were not only present as a simple coating, as there is no evidence of proteins in the washing solutions. Only with the combination of a strong detergent (SDS), a reducing agent (mercaptoethanol) and high temperature (100° C.) could amelogenins be extracted from the surface layer of the titanium hydride. The amount of protein extracted was calculated to range between 57 and 114 µg/cm$^2$ with a mean value of 87 µg amelogenin per cm$^2$, by comparison with the amelogenin standard. This figure is well within the bioactivity range of this extracellular matrix protein. Identical control implants that had been present is the same electrolytic cell as the experimental implants, but which were not connected to the cathode, showed no significant amounts of amelogenin proteins attached to the surface (<1 µg/cm$^2$).

EXAMPLE 3

Production of a nucleic acid-containing titanium hydride implant surface layer.

The set-up from example one was used to produce a layer of titanium hydride containing nucleic acids in the form of radiolabeled total human placenta DNA onto electropolished titanium implants with a total surface area of 0.35 cm$^2$ exposed to the electrolyte. The electrolyte in both chambers was 1 M NaCl in sterile water. The pH was adjusted to pH 2 by the use of HCl. The initial concentration of DNA in the electrolyte was 10 µg/ml. For electrolysis a voltage of 10 volts at a charge density of 1 mA/cm$^2$ and a $T_{cat}$ of 75° C.

were used. Electrolysis was allowed to progress for 16 or 24 hours after which the titanium specimens were removed from the electrolysis cell, rinsed three times in ample amounts of Tris-EDTA buffer (TE-buffer; 10 mM Tris-Cl and 1 mM EDTA in sterile water, pH 7,6) and then allowed to air dry over night in a desiccator.

The DNA was radiolabeled using a Stratagene Prime-It® II Random Primer Labeling kit for production of high specific-activity probes and [α-$^{32}$P]dATP (Amersham). After labeling of the DNA, the specific radioactivity of the DNA probe was measured in a Packard Tricarb® scintillation counter to be 3.0×10$^8$ disintegrations per minute per microgram labeled DNA (dpm/µg).

After drying the titanium specimens with tentative nucleic acids attached, were put on a phosphor screen (Fujii®) for 15 minutes. The specimens were then removed and the phosphor screen was scanned in a BioRad® phosphor imaging machine measuring the number of disintegrations occurred at the surface of each implant using a 100 µm grid (12265 points per implant) The experiment was repeated twice in a series of 16 implants, both times with 5 negative internal controls in the form of identical titanium implants that was present in the reaction chamber during the whole process, but which were not connected to the cathode. For the first series the reaction time was 24 hours, for the second it was 16 hours. The total number of dpm per implant was calculated and converted to µg DNA per square centimeter (µg DNA/cm$^2$).

The amount of DNA present on the implants ranged between 0.25 and 0.75 µg/cm$^2$ with a mean value of 0.43 µg DNA per cm$^2$ when the reaction time was 24 hours. When the reaction time was reduced to 16 hours, the respective values ranged between 0.19 and 0.32 µg/cm$^2$ with a mean value of 0.30 µg DNA per cm$^2$. This figure is well within the applicable range for gene therapy and DNA vaccines and other molecular medicine applications. Identical control implants that had been present is the same electrolytic cell as the experimental implants, but that were not connected to the cathode showed only very small amounts (picograms) of DNA attached to the surface.

This experiment clearly demonstrates that a significant amount of DNA was incorporated in the hydride layer during the electrolytic process. The DNA was not merely present as a simple coating because the DNA was not dissolved or washed off the test implants during rinsing with TE. Furthermore, the fact that the amount of DNA incorporated in the titanium hydride surface layer increased linearly with reaction time also shows that adjusting reaction time is an easy way to control the amount of biomolecules in the hydride layer.

EXAMPLE 4

Preparation of a titanium hydride implant surface layer containing ascorbic acid The set-up from Example 1 was used to prepare a layer of titanium hydride containing ascorbic acid (vitamin C) onto electropolished coin-shaped titanium implants with a total surface area exposed to the electrolyte of 0.35 cm$^2$. The electrolyte in both chambers was saline with pH adjusted to pH 3 by means of phosphoric acid. The initial concentration of ascorbic acid was 10 mg/ml. Electrolysis with a voltage of 6 volts at a current density of 2 mA/cm$^2$ and a cathode chamber temperature of 20° C. was used. Electrolysis was allowed to progress for 16 hours after which the titanium implant is removed from the electrolysis cell, rinsed twice in sterile water and allowed to dry in a desiccator.

After drying over night the tentative ascorbic acid was dissolved from the titanium specimens by submerging the specimens in 1 ml Tris-EDTA buffer (TE-buffer; 10 mM Tris-Cl and 1 mM EDTA in sterile water) at pH 8.0 for 1 hour with shaking. The amount of ascorbic acid in the buffer samples was then analyzed by measuring light absorption at 250 nm and comparing the results with a standard curve for ascorbic acid in TE, pH 8,0 at this wavelength. Identical control implants present is the same electrolytic cell as the experimental implants, but not connected to the cathode may be used as controls. The experiment was repeated twice in a series of 16 implants, both times with 5 negative, internal controls.

The amount of ascorbic acid extracted from the titanium specimens was calculated to range between 28 and 76 $\mu g/cm^2$ with a mean value of 39 $\mu g$ ascorbic acid per $cm^2$, by comparison with the ascorbic acid standard. This figure is well within the bioactivity range of this vitamin (the normal plasma concentration in humans range between 8–15 $\mu g/ml$). The internal control specimens that had been present is the same electrolytic cell as the experimental implants, but which were not connected to the cathode, showed only minute amounts of ascorbic acid attached to the surface (<4 $\mu g/cm^2$). This experiment clearly demonstrates that a biologically significant amount of ascorbic acid can be incorporated or attached to the titanium hydride layer during the electrolytic process.

EXAMPLE 5

Preparation of a titanium hydride implant surface layer containing a synthetic growth factor-based peptide The set-up from Example 1 may be used to prepare a layer of titanium hydride containing a synthetic, full-length (37 amino acids) fibroblast growth factor 4 (FGF-4) peptide onto coin-shaped electropolished titanium implants with a total surface area of 0.6 $cm^2$ exposed to the electrolyte. Electrolytes, pH, voltage, current density and electrolysis time may suitably be as in Example 1. The initial concentration of FGF-4 may suitably be 0.1 mg/ml, and the cathode chamber temperature may suitably be 50° C.

Following washing in saline and 2×SDS-PAGE buffer, precipitation, centrifugation, re-dissolution in SDS-PAGE, boiling and electrophoresis as in Example 1, protein in the gel may be transferred to a silver staining solution and the full-length synthetic FGF-4 peptides present visualised as a distinct band in the gel. Identical control implants incorporated in the same electrolytic cell as the experimental implants, but not connected to the cathode, can be used as controls.

EXAMPLE 6

Preparation of a titanium hydride implant surface layer containing an antibiotic The set-up from Example 1 may be used to prepare a layer of titanium hydride containing the antibiotic agent amoxicillin (aminopenicillinium) onto an electropolished, coin-shaped titanium implant with a surface area exposed to the electrolyte of 0.6 $cm^2$. The electrolyte in both chambers is suitably 1M NaCl in sterile water with pH adjusted to pH 2 by means of HCl, and the initial concentration of amoxicillin is suitably 5 mg/ml. For electrolysis a voltage of 10 volts at a charge density of 1 $mA/cm^2$ and a cathode chamber temperature of 50° C. may be used. Electrolysis may suitably be allowed to progress for 24 hours after which the titanium implant is removed from the electrolysis cell, rinsed in sterile water and allowed to dry in a desiccator.

After drying the amount of amoxicillin trapped in the hydride layer on the titanium implants may be assessed by its antibacterial effect on penicillin sensitive bacteria of the species *Escherichia coli* (*E. coli*), strain K12, in liquid cultures. The cultures are suitably inoculated with one colony of *E. coli* K12 in 5 ml LB broth. After inoculation the modified implants and controls are placed in the culture and the cultures incubated at 37° C. over-night. The next day the amounts of bacteria present in the cultures may be assessed by photometry and comparison with a standard dilution. Identical control implants present in the same electrolytic cell as the experimental implants, but not connected to the cathode may be used as controls.

EXAMPLE 7

Preparation of a biomineral-inducing titanium hydride implant surface layer

The set-up from Example 1 may be used to prepare a layer of titanium hydride containing a synthetic poly-proline peptide that has the potential to act as a biological nucleator of mineral formation in saturated solutions of calcium phosphate. The biomolecule may be incorporated in the hydride layer on electropolished, coin-shaped titanium implants surface with a total area exposed to the electrolyte of 0.6 $cm^2$. The electrolyte in both chambers may suitably be 1M NaCl in sterile water with pH adjusted to pH 2 by means of HCl, and the initial concentration of the synthetic poly-proline ma suitably be 0,1 mg/ml. For electrolysis a voltage of 10 volts at a current density of 1 $mA/cm^2$ and a cathode chamber temperature of 70° C. may be used. Electrolysis may suitably be allowed to progress for 18 hours after which the titanium implants are removed from the electrolysis cell, rinsed in sterile water and allowed to air-dry in a desiccator.

After drying the titanium implants and controls with tentative mineral nucleating peptide attached are placed in 5 ml saturated solution of calcium phosphate. After incubation for 4 hours in room temperature, the implants are removed from the mineral solution, rinsed in sterile water and air-dried in a desiccator. When dry, the implants may be directly submitted to scanning electron microscopy for assessment of the number of mineral foci present on the modified surfaces. Identical control implants present is the same electrolytic cell as the experimental implants but not connected to the cathode may be used as controls.

EXAMPLE 8

Preparation of a swelling (space filling) biomolecule-titanium-hydride implant surface layer.

The set-up from Example 1 may be used to prepare a layer of titanium hydride containing Ca-alginate nanospheres (Pronova AS) onto electropolished, coin-shaped titanium implants with a total area exposed to the electrolyte of 0.6 $cm^2$. The electrolyte in both chambers is suitably 1M $CaCl_2$ in sterile water with pH adjusted to pH 5,5 by means of HCl, and the initial concentration of Ca-alginate is suitably 1% w/v. For electrolysis a voltage of 10 volts at a current density of 1 $mA/cm^2$ and a cathode chamber temperature of 35° C. may be used. Electrolysis is suitably allowed to progress for 48 hours after which the titanium implants are removed from the electrolysis cell, rinsed in cold sterile water and allowed to air-dry in a desiccator.

After drying, the titanium implants with a hydride-alginate layer are suitably submerged in sterile saline, dyed with bromophenol blue (0,02 g/ml) and incubated for one hour at 37° C. with the modified surface facing the solution. Following incubation in the dyed saline the implants and controls are rinsed in distilled water and observed with a magnifying glass for the retention of blue dye within the tentative swelled alginate layer. The thickness of the alginate layers may also be assessed by viewing the implants edge on in a calibrated light microscope. Identical control implants present is the same electrolytic cell as the experimental implants but not connected to the cathode may be used as controls.

EXAMPLE 9

Preparation of a dual layer biomolecule-titanium-hydride implant surface

The set-up from Example 1 may be used to prepare a dual layer of biomolecule containing titanium hydride on the surface of electropolished, coin-shaped titanium implants with a total surface exposed to the electrolyte of 0.6 cm$^2$. The inner layer may be prepared using amelogenin as biomolecule according to the method in Example 1. Immediately after this procedure, and without air-drying in between, the electrolyte and conditions may be changed to those of Example 3 using genomic human DNA as biomolecule. In this way titanium implants may be prepared with an outer layer of titanium hydride-DNA overlaying an inner layer of titanium hydride-amelogenin. After the electrolysis the implants are removed from the electrolysis cell, rinsed in sterile water and allowed to air-dry in a desiccator.

After drying the titanium specimens with tentative nucleic acids and proteins attached are suitably rinsed three times in Tris-EDTA buffer (TE-buffer; 10 mM Tris-Cl and 1 mM EDTA in sterile water). At each rinse the pH is increased starting at pH 7,4, then rinsed at pH 7,6 and finally at pH 8.0. After rinsing in TE the remaining DNA and protein on the titanium implants is finally removed using 0.1 N NaOH. The rinsing fractions are then divided in two; on part for nucleic acid analysis and one for protein analysis. The DNA fractions are suitably precipitated with an equal volume of absolute alcohol at −20° C. for 1 hour and then cleared from the supernatant by centrifugation at 13.000 g at 4° C. The pellet is then dissolved in 50 µl TE buffer pH 7.4 and the amount of DNA from all four rinsing solutions assessed by fluorometric analysis using Hoechst dye (Boehringer Mannheim).

The fractions for protein analysis are suitably precipitated with an equal volume of 0,6 N perchloric acid and the supernatants cleared by centrifugation. The precipitation pellets containing salt and proteins are then dissolved in 50 µl 2×SDS-PAGE sample buffer (0,4 g SDS, 1,0 g 2-mercaptoethanol, 0,02 g bromophenol blue and 4,4 g glycerol in 10 ml 0,125 M Tris/HCl, pH 6,8) and boiled for five minutes. All samples are then submitted to electrophoresis on a 10% SDS-polyacrylamide gel at 80 mA for 4 hours. After electrophoresis proteins in the gel are transferred to a silver staining solution and amelogenin present in the fractions is visualized as distinct bands in the gel. Identical control implants present is the same electrolytic cell as the experimental implants but not connected to the cathode may be used as controls.

EXAMPLE 10

Preparation of a dual zone biomolecule-titanium-hydride layered implant surface.

The set-up from Example 1 may be used to prepare two separate zones of titanium hydride layers. Electropolished, rod-shaped titanium implants with a total area of 2 cm$^2$ were treated according to examples 3 and 6. First the implants were placed in the electrolyte from example 3, so that only one half of each implant was submerged in the electrolyte. After the procedure of example 3 was completed, the implants were turned around and placed in a new electrolyte similar to the one used in example 6, so that the untreated half of each implant now was submerged in electrolyte. The procedure and reaction conditions from examples 6 were then carried out, after which the titanium specimen was removed from the electrolysis cell, rinsed in sterile water and allowed to dry in a desiccator.

Following electrolysis the dual zone implants are cut in two at the center. The halves layered with titanium hydride-synthetic FGF-4 peptide may be submitted to analysis according to Example 2. The other halves of the implants, layered with titanium hydride-amoxicillin, may be analyzed in the bacterial growth assay according to Example 5. Identical control implants present is the same electrolytic cells as the experimental implants but not connected to the cathode may be used as controls.

EXAMPLE 11

Preparation of a osteoinductive titanium hydride implant surface layer containing a biomolecule Implants prepared as in Example 1 (titanium hydride—amelogenin) are placed in calibrated bone defects in the tibia bone of rabbits, making sure that fenestrations into the bone marrow beneath the implants allow migration of osteogenic cells to the modified implant surfaces, using a standardized and validated model (Rønold and Ellingsen, European Society for Biomaterials Conference, Amsterdam, October 2000). On the day after surgery and every following week the rabbits are given an intravenous calcein (Sigma) injection of 10 mg/kg body weight. At four weeks after placing of the modified implants and control implants the rabbits will be sacrificed and the tibia removed, fixed in 4% formaldehyde and embedded for preparation of ground sections through the bone and the integrated implant material. Identical control implants present is the same electrolytic cell as the experimental implants but not connected to the cathode may be used as controls.

The invention claimed is:

1. A medical prosthetic device or medical implant comprising a metal material selected from the group consisting of titanium or an alloy thereof, zirconium or an alloy thereof, tantalum or an alloy thereof, hafnium or an alloy thereof, niobuim or an alloy thereof and a chromium-vanadium alloy,
   wherein surface parts of the metal material comprise a layer of a corresponding hydride material selected from the group consisting of titanium hydride, zirconium hydride, tantalum hydride, hafnium hydride, niobium hydride, chromium hydride, vanadium hydride, and chromium-vanadium hydride,
   wherein the layer of hydride material comprises one or more biomolecule substances, said biomolecule substance being an ampholyte.

2. A medical prosthetic device or medical implant comprising a metal material selected from the group consisting of titanium or an alloy thereof, zirconium or an alloy thereof, tantalum or an alloy thereof, hafnium or an alloy thereof, niobuim or an alloy thereof and a chromium-vanadium alloy, wherein surface parts of the metal material comprise a layer of a corresponding hydride material selected from the group consisting of titanium hydride, zirconium hydride, tantalum hydride, hafnium hydride, niobium hydride, chromium hydride, vanadium hydride, and chromium-vanadium hydride, and wherein the layer of hydride material comprises one or more biomolecule substances, said biomolecule substance exhibiting a net positive charge dissolved in a salt solution having an ionic strength within the range of from 0.01 to 10 M, a temperature within the range of from 20 to 100° C., and a pH within the range of from 0 to 10.

3. A device or implant as claimed in claim 1 or 2, wherein the metal material is titanium or an alloy thereof.

4. A device or implant as claimed in claim 1 or 2, wherein the biomolecule substance. is selected from the group consisting of natural or recombinant bio-adhesives; natural or recombinant cell attachment factors; natural, recombinant or synthetic biopolymers; natural or recombinant blood proteins; natural or recombinant enzymes; natural or recombinant extracellular matrix proteins; natural or synthetic extracellular matrix biomolecules; natural or recombinant growth factors and hormones; natural, recombinant or synthetic peptide hormones; natural, recombinant or synthetic deoxyribonucleic acids; natural, recombinant or synthetic ribonucleotide acids; natural or recombinant receptors; enzyme inhibitors; drugs; biologically active anions and cations; vitamins; adenosine monophosphate (AMP), adenosine diphosphate (ADP) or adenosine triphosphate (ATP); marker biomolecules; amino acids; fatty acids; nucleotides (RNA and DNA bases); and sugars.

5. A device or implant as claimed in claim 1 or 2, wherein the biomolecule substance is interlocked, bound, trapped and/or integrated in or with the hydride material.

6. A device or implant as claimed in claim 1 or 2, wherein the layer of the hydride material comprises one or more biomolecule substances in an amount of about 1 picogram per mm$^2$ to 1 mg per mm$^2$.

7. A device or implant as claimed in claim 1 or 2, wherein said surface parts of the metal material comprising the layer of the hydride material is adapted to be in contact with bone or other tissue when the device is deployed in the body of a mammal.

8. A device or implant as claimed in claim 1 or 2, selected from the group consisting of: a prosthetic femoral hip joint; a prosthetic femoral head; a prosthetic acetabular cup; a prosthetic elbow; a prosthetic knee; a prosthetic shoulder; a prosthetic wrist; a prosthetic ankle; a prosthetic hand; a prosthetic finger; a prosthetic toe; a prosthetic vertebrae; a prosthetic spinal disc; a prosthetic cochlea; a prosthetic vessel; and a prosthetic heart valve.

9. A device or implant as claimed in claim 3, wherein the material is titanium.

10. A device or implant as claimed in claim 6, wherein the layer of the hydride material comprises one or more biomolecule substances in an amount of about 0.1 nanogram per mm$^2$ to 100 microgram per mm$^2$.

11. A device or implant as claimed in claim 1 or 2, wherein said device or implant is selected from the group consisting of: an artificial joint, a dental implant, an ossiculoplastic implant, a middle ear implant, a cochlcar implant, an orthopaedic fixation device, a pacemaker, a catheter, a space filling implant, an implant for retention of hearing aids, an implant for external fixation, an intrauterine device (IUD) and a bioelectric device.

12. A device or implant as claimed in claim 8, wherein said prosthetic elbow implant is adapted to replace a stem, wedge or articular insert.

13. A device or implant as claimed in claim 8, wherein said prosthetic knee implant is adapted to replace a femoral component, a tibial component, stem, wedge, an articular insert or a patellar component.

14. A device or implant as claimed in claim 8, wherein said prosthetic shoulder implant is adapted to replace a stem or head.

15. A device or implant as claimed in claim 11, wherein said middle ear knee implant is adapted to replace an incus, a malleus, a stapes, an incus-stapes, a malleus-incus, or a malleus-incus-stapes.

16. A device or implant as claimed in claim 11, wherein said orthopaedic fixation device is a nail, screw, staple or plate.

17. A device or implant as claimed in claim 11, wherein said bioelectronic device is an intracochlear or intracranial electronic device.

18. A device or implant as claimed in claim 1 or 2, wherein said device or implant is sterile.

* * * * *